United States Patent
Raymond (10) Patent No.: US 6,856,408 B2
(45) Date of Patent: Feb. 15, 2005

(54) LINE PROFILE ASYMMETRY MEASUREMENT USING SCATTEROMETRY

(75) Inventor: Christopher J. Raymond, Albuquerque, NM (US)

(73) Assignee: Accent Optical Technologies, Inc., Bend, OR (US)

( * ) Notice: Subject to any disclaimer, the term of this patent is extended or adjusted under 35 U.S.C. 154(b) by 211 days.

(21) Appl. No.: 10/086,339

(22) Filed: Feb. 28, 2002

(65) Prior Publication Data

US 2002/0149782 A1 Oct. 17, 2002

Related U.S. Application Data

(60) Provisional application No. 60/273,039, filed on Mar. 2, 2001.

(51) Int. Cl.[7] .......................... G01B 11/02; G01N 21/88
(52) U.S. Cl. ..................... 356/601; 356/636; 356/237.5
(58) Field of Search ................................ 356/601, 625, 356/636, 237.4, 237.5

(56) References Cited

U.S. PATENT DOCUMENTS

| | | |
|---|---|---|
| 4,933,567 A | 6/1990 | Silva et al. |
| 4,978,862 A | 12/1990 | Silva et al. |
| 5,114,233 A | 5/1992 | Clark et al. |
| 5,144,150 A | 9/1992 | Yoshizumi et al. ......... 250/561 |
| 5,241,369 A | 8/1993 | McNeil et al. |
| 5,313,542 A | 5/1994 | Castonguay |
| 5,475,617 A | 12/1995 | Castonguay |
| 5,637,873 A | 6/1997 | Davis et al. |
| 5,640,246 A | 6/1997 | Castonguay |
| 5,682,466 A | 10/1997 | Maeda et al. |
| 5,703,692 A | 12/1997 | McNeil et al. |
| 5,739,909 A | 4/1998 | Blayo et al. |
| 5,864,394 A | 1/1999 | Jordan, III et al. |
| 5,867,276 A | 2/1999 | McNeil et al. |
| 5,889,593 A | 3/1999 | Bareket |
| 5,905,573 A | 5/1999 | Stallard et al. |
| 5,912,741 A | 6/1999 | Carter et al. |
| 5,963,329 A * | 10/1999 | Conrad et al. .............. 356/613 |
| 5,982,489 A | 11/1999 | Shiraishi |
| 6,075,594 A | 6/2000 | Thomas et al. |
| 6,212,010 B1 | 4/2001 | Iizuka et al. |
| 6,292,259 B1 | 9/2001 | Fossey et al. |
| 6,292,265 B1 | 9/2001 | Finarov et al. |

(List continued on next page.)

FOREIGN PATENT DOCUMENTS

| | | |
|---|---|---|
| JP | 03-255907 | 11/1991 |
| JP | 06-317412 | 11/1994 |
| JP | 2001-074636 | 3/2001 |
| WO | WO 02/065545 A2 | 8/2002 |
| WO | WO 02/069390 A2 | 9/2002 |

OTHER PUBLICATIONS

U.S. Provisional application No. 60/268,485, filed Feb. 12, 2001, Sezginer et al.
U.S. Provisional application No. 60/295,111, filed Jun. 1, 2001, Sezginer et al.
U.S. Provisional application No. 60/322,219, filed Sep. 14, 2001, Sezginer et al.

Primary Examiner—Richard A. Rosenberger
(74) Attorney, Agent, or Firm—Jeffrey D. Myers; Stephen A. Slusher; Peacock, Myers & Adams, P.C.

(57) ABSTRACT

A method of and apparatus for measuring line profile asymmetries in microelectronic devices comprising directing light at an array of microelectronic features of a microelectronic device, detecting light scattered back from the array comprising either or both of one or more angles of reflection and one or more wavelengths, and comparing one or more characteristics of the back-scattered light by examining data from complementary angles of reflection or performing a model comparison.

56 Claims, 9 Drawing Sheets

U.S. PATENT DOCUMENTS

| | | |
|---|---|---|
| 6,538,731 B2 | 3/2003 | Niu et al. |
| 2002/0038196 A1 | 3/2002 | Johnson et al. |
| 2002/0135781 A1 | 9/2002 | Singh et al. |
| 2002/0135875 A1 | 9/2002 | Niu et al. |
| 2002/0158193 A1 | 10/2002 | Sezginer et al. |
| 2002/0182760 A1 | 12/2002 | Wack et al. |
| 2003/0002043 A1 | 1/2003 | Abdulhalim et al. |
| 2003/0042579 A1 | 3/2003 | Schultz |
| 2003/0043372 A1 | 3/2003 | Schultz |
| 2003/0044702 A1 | 3/2003 | Schulz |
| 2003/0143761 A1 | 7/2003 | Fukuda |

* cited by examiner

LINE PROFILE ASYMMETRY MEASUREMENT USING SCATTEROMETRY

CROSS-REFERENCE TO RELATED APPLICATIONS

This application claims the benefit of the filing of U.S. Provisional Patent Application Ser. No. 60/273,039, entitled "Process Qualification by the Measurement of Line Profile Asymmetry Using Scatterometry", filed on Mar. 2, 2001, and the specification thereof is incorporated herein by reference.

BACKGROUND OF THE INVENTION

1. Field of the Invention (Technical Field)

The present invention relates to optical inspection of microelectronic devices, in particular measurement of line profile asymmetry using scatterometry.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The fabrication of a microelectronic device is a complicated procedure that uses a variety of equipment for the different process steps involved. First, the lithography process transfers the image being made into a light sensitive material known as photoresist. This image in photoresist, in turn, acts as a mask for the next patterning process known as etching. Etching is the process by which the resist image is transferred into a suitable material such as poly-silicon. Then the etched material is over-filled with some insulating materials, planarized if necessary, and the whole process begins again.

Throughout the entire process the devices being made should be symmetric in nature from step to step, i.e., a transistor gate if manufactured correctly will have equal left and right sidewalls as well as other features such as, but not limited to, equal left and right corner rounding. If errors occur during the processing this desired symmetry may be compromised, and as a result the device integrity or functionality may also be compromised. If the asymmetry is quite severe the device may not function at all.

The present invention is of a manner of performing symmetry/asymmetry measurements via scatterometry. Scatterometry is an optical inspection technique well suited for the measurement of symmetry or asymmetry on microelectronic devices. By analyzing the light scattered from an array of microelectronic features, measurements of the line profile can be made. In particular, a scatterometer that measures at complementary angles, i.e., +45 degrees from a position perpendicular to the surface and −45 degrees, is ideally suited for symmetry/asymmetry measurements because the reflectance properties of the line profile can vary at these angles, although complementary angles are not necessarily needed to detect asymmetry. To enhance the sensitivity of this effect the array of features should be placed in a particular orientation, known throughout the specification and claims as a general conical configuration, namely one in which the wave vector of the illuminating beam does not remain parallel to the array's plane of symmetry.

Prior art techniques typically employ "classic" scattering. These are measurements geared towards the measurement of surface roughness, defects, pitting, etc. However, the present invention is based on the physics of diffraction, with the measurements in the invention always occurring with respect to periodic features (such as line/space gratings).

Prior work in scatterometry used the technique for the measurement of line profiles in resist and etched materials. C. J. Raymond, et al., "Resist and etched line profile characterization using scatterometry," *Integrated Circuit Metrology, Inspection and Process Control XI, Proc. SPIE* 3050 (1997). The present invention provides a technique for the measurement of asymmetric line profiles (e.g., unequal sidewall angles).

U.S. Pat. No. 5,963,329 discloses an analysis method used to obtain a scatterometry measurement. The comparison between the diffraction model and the measured signature data is typically done by pre-computing a series of modeled signatures and storing them in a library. Then, the measured signature is compared to the library of modeled signatures to determine the parameters of interest. The patent essentially discloses a real-time model regression, where the signature iterations are performed in real-time and the model is changed repeatedly until a satisfactory match is obtained. However, there is no disclosure of using such a technique to determine asymmetry. Note that the profiles in FIG. 2 and FIG. 4 are symmetric, and column 7, line 40, reads ". . . and to define the separation between the symmetric left and right edge profiles . . ."

U.S. Pat. No. 6,292,265 is concerned with measuring dishing, erosion and residue by way of monitoring the thickness of materials that are prone to these effects. Note column 3, line 15, which reads: "It is a major feature of the present invention to provide such a method . . . to prevent residues, dishing and erosion effects." Note also column 3, paragraph 25, which reads: "The main idea of the present invention is based on . . . an optical monitoring system capable of thickness measurements in patterned structures." The disclosure concerns CMP, which is a thickness/relief measurement, instead of the measurement of a full line profile and any asymmetries that may be present.

U.S. Pat. No. 5,912,741 pertains to measurements of surface microstructure/roughness and is based on classical scattering. The present invention is based on measuring a specific diffraction order—this patent is based on measuring diffuse reflectance or specular reflectance and not diffraction. There is also no mention of asymmetry measurements—this is because this measurement is not applied to line profile measurements.

U.S. Pat. Nos. 4,978,862 and 4,933,567 are also geared towards microstructure or microdefects in materials and not for physical line profile measurements. Crystalline defects and impurities that could be measured are discussed. There is no discussion about the measurement of diffraction intensity and how it could be used for the measurement of asymmetric line profiles.

U.S. Pat. No. 6,292,259 also relates to classical scattering measurements, such as that induced by pits and particles on the surface of a material. The novelty of this patent is that it can distinguish pits from particles, but it does not concern diffraction or diffraction intensity measurements.

U.S. Pat. No. 5,889,593 discloses an optical design that is capable of an angular dependent measurement. The patent discloses an optical imaging array (reference 60 in the figures). It does not discuss the importance of using complementary angles for the measurement of line profile asymmetry. In fact, the repeated line structures shown in FIG. 6 are symmetric.

U.S. Pat. No. 5,905,573 relates to the perturbation of an evanescent field that is formed in a waveguide/resonator. The local presence of topography on a material being examined causes a perturbation of the probing radiation and hence a 'blip' in the intensity of the probing radiation. This measurement is not based on the physics of diffraction. It is also not an angle-dependent intensity measurement—if the power of the radiation in the resonator increases or decreases, then there must be some topography present that is perturbing the field. Furthermore, there is no discussion of asymmetry measurements.

U.S. Pat. No. 5,982,489 relates to depth measurement only and not line profile (so it is not possible to determine line profile asymmetry). It is also based on an interference technique as opposed to a diffraction/scattering measurement.

U.S. Pat. No. 5,864,394 also relates to defect measurements. Column 1, line 35, reads: ". . . for inspecting anomalies (contaminant particles and pattern defects) on surfaces." There is no mention of diffraction measurements and hence no discussion of the measurement of line profiles, much less any asymmetry that might be present.

U.S. Pat, No. 5,637,873 pertains to an optical design with applications to the emissivity/reflectance of surfaces and coatings. This is not a patent with applications to patterned features or the measurement of the profiles of those patterned features.

U.S. Pat. Nos. 5,313,542, 5,475,617 and 5,640,246 pertain mainly to an optical design that allows for the measurement of partial or full hemispherically scattered light. The applications of this design are to measure light scatter caused by scratches, blemishes, bubbles, subsurface defects, and surface roughness, and are classic light scattering applications. There is no mention of measuring diffraction for the purposes of line profile measurements, and no discussion of asymmetry.

An NMRC Scientific Report regarding Photonics Research from 1999 is also related strictly to classic scattering applications (i.e., the measurement of surface defects). While it does involve an angular scattering measurement, it does not measure diffraction and hence is not applied for line profile measurements.

P. Ding, et al., "Light Scattering Study of Roughness and Dishing on Post-CMP Wafers" (date unknown) is also geared towards classic scattering. The measurement itself is an angular scattering measurement and does involve the measurement of diffraction (the samples are periodic lines and spaces). However, the measurement data is geared towards roughness and dishing applications, and does not involve a comparison to a theoretical diffraction model. It therefore does not measure the line profiles and hence no mention of asymmetry measurements is made.

"2pi Steradian Detection of Pits" (date unknown) relates to sub-surface defects and this literature is thus related to classic scattering applications. The hardware employed is an angle resolved scatterometer, but unless such hardware is coupled with a diffraction model and an analysis method, the measurement of line profile asymmetry cannot be performed.

SUMMARY OF THE INVENTION (DISCLOSURE OF THE INVENTION)

The present invention is of a method of and apparatus for measuring line profile asymmetries in microelectronic devices, comprising: directing light at an array of microelectronic features of a microelectronic device; detecting light scattered back from the array comprising one or more features selected from the group consisting of one or more angles of reflection and one or more wavelengths; and comparing one or more characteristics of the back-scattered light by performing an operation selected from the group consisting of examining data from complementary angles of reflection and performing a model comparison. In the preferred embodiment, the directed light may be at either substantially a single wavelength or a plurality of wavelengths. Light intensity may be compared, with optional addition of comparison of phase. Ratios of light magnitude and light phase may be compared. Preferably the light is directed at an array of microelectronic features in general conical configuration, directing and detecting are by an angular scatterometer, comparing comprises decomposing back-scattered light into S and P components relative to a plane of incidence, and detecting is of specular order diffracted light. Preferably, the results of the comparison are used to detect asymmetries within a single layer of the microelectronic device or asymmetries within multiple layers of the microelectronic device. A manufacturing process can then be appropriately controlled if results of the comparison indicate an asymmetry in the array.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 11 (a) and (b) are, respectively, left and right sidewall angle comparisons between scatterometry and cross-section SEM for the 193 nm resist wafer;

DESCRIPTION OF THE PREFERRED EMBODIMENTS

Best Modes for Carrying out the Invention

The present invention is of a method of measuring symmetry/asymmetry of an array of microelectronic features. By analyzing the light scattered from an array of microelectronic features, measurements of the line profile can be made. In particular, a scatterometer that measures at complementary angles, i.e., +45 degrees from a position perpendicular to the surface and −45 degrees, is ideally suited for symmetry/asymmetry measurements because the reflectance properties of the line profile can vary at these angles, although complementary angles are not necessary for the measurement of asymmetry. To enhance the sensitivity of this effect the array of features is preferably placed in a particular orientation, known as a general conical configuration.

The scatterometry measurements of the invention can be performed at any complementary angles (+/−45 degrees is an example), and may include several angles or a series of angles. Furthermore, measurements at each angle may include light of a single wavelength (such as a laser), or may include light composed of several wavelengths or broad wavelength light (such as a white light source). The intensity of the light alone might be measured, or the intensity and phase can be measured in tandem, similar to an ellipsometry measurement.

Regardless of the light source used or the manner in which it is measured, assuming the array is oriented in the general conical configuration, it is the comparison of data from complementary angles that will immediately show if an asymmetry is present. Without any additional need for analysis, if the light measurements are the same then the profile is symmetric. Conversely, if the light measurements differ then the profile is asymmetric. In general, as more complementary angles are used, the better the measurement sensitivity. This makes angular scatterometers (those that scan through angle) better suited than spectral scatterometers (those that scan through wavelength) for these measurements of profile asymmetry.

Applications of the complementary angle scatterometry method of the invention include, but are not limited to:

alignment of a wafer stage with an optical system, such as that on a lithography tool (stepper or scanner) or in a lithography process;

alignment of wafer with an optical system, such as that on a lithography tool (stepper or scanner) or in a lithography process determination of the lens aberrations present in a lithography tool or process;

general diagnostic of the imaging performance of a lithography tool or process;

measurement of the temperature uniformity of a bake process/station;

measurement of the thickness uniformity of resist spin coaters or spin processing;

measurement of the uniformity of a developer process/station;

characterization of an etch tool or process;

characterization of a planarization tool or process; and characterization of a metallization tool or process.

Control of any of the aforementioned processes

In the most general sense, one goal of semiconductor processing is to produce a device (i.e., a transistor gate) that is inherently symmetric. Indeed, it is rare that a device is produced that in intentionally non-symmetric or asymmetric. To this end the lithography patterning process is geared towards symmetry, particularly with regards to footing at the bottom of a line and equivalent sidewalls. Likewise, etch processing also strives to produce symmetric features, in this case mostly with respect to line sidewalls. For control of either of these processing steps, then, measurement techniques must be able to detect asymmetry, and preferably be able to measure any asymmetry present (such as unequal left and right sidewalls).

Scatterometry is an optical metrology based on the analysis of light scattered from a periodic array of features. In a strict physical sense, this light 'scattered' from a periodic sample is actually due to diffraction, but in a general sense it is termed scatter. When a series of periodic features (known as a diffraction grating) is illuminated with some light source, the reflectance properties of the scattered/diffracted light depends on the structure and composition of the features themselves. Therefore, by analyzing the scatter 'signature' one can determine the shape and dimensions of the diffraction grating.

Figure 1:
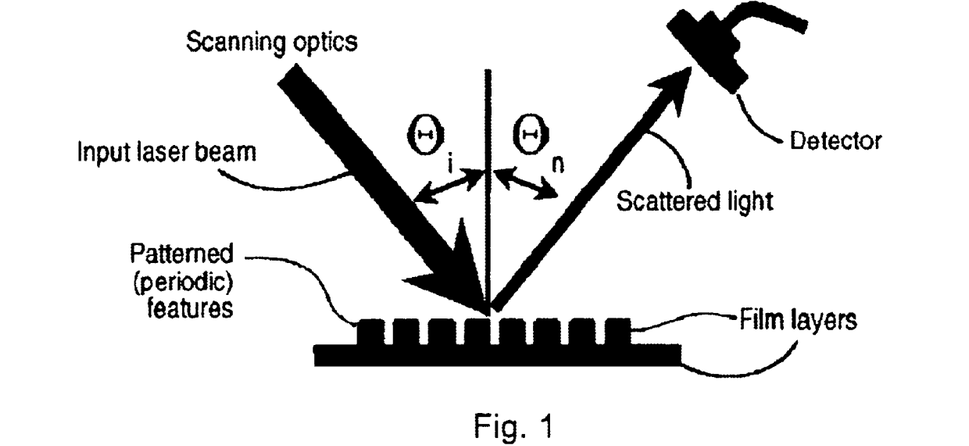
FIG. 1 is a block diagram of the angular scatterometer employed in the present invention.

Diffraction can actually give rise to a number of different 'orders,' or light beams, scattered from the features. But for modern semiconductor production geometries the period of the features is small and therefore typically only one diffraction order exists. This order is known as the 'specular' or 'zero$^{th}$' order and is the light beam most frequently used in scatterometry technology. One of the more common ways of analyzing light scatter using the specular order is to vary the incidence angle of the illuminating light source (which is usually a laser). As FIG. 1 illustrates, as the incident angle $\Theta_i$ is varied and a detector moves in tandem at angle $\Theta_n$ to measure the diffracted power of the specular order, a scatter 'signature' is measured. It is this scatter signature—known as an angular signature—that contains information about the diffracting structure, such as the thickness of the grating and the width of a grating line. This angular signature, when measured properly, can also contain information about any asymmetry present in the grating lines as well. By measuring through complementary angles (both positive and negative with respect to normal), a signature can be obtained that is asymmetric if the line is asymmetric. Conversely, if the line profile is in fact symmetric, the measured signature will also be symmetric. Complementary angles are not needed, however, if a suitable theoretical diffraction model is available for comparison purposes, and the 'inverse' problem (see below) can be performed.

The scatterometry method is often described in two parts, typically known as the 'forward' and 'inverse' problems. In the simplest sense the forward problem is the measurement of a scatter signature, and the inverse problem is the analysis of the signature in order to provide meaningful data. Although many types of scatterometers have been investigated over the years, e.g., C. J. Raymond, et al., "Metrology of subwavelength photoresist gratings using optical scatterometry," *Journal of Vacuum Science and Technology B* 13(4), pp. 1484–1495 (1995); S. Coulombe, et al., "Ellipsometric scatterometry for sub 0.1 μm measurements," *Integrated Circuit Metrology, Inspection and Process Control XII, Proc. SPIE* 3332 (1999); Z. R. Hatab, et al., "Sixteen-megabit dynamic random access memory trench depth characterization using two-dimensional diffraction analysis," *Journal of Vacuum Science and Technology B* 13(2), pp. 174–182 (1995); and X. Ni, et al., "Specular spectroscopic scatterometry in DUV lithography," *Proc SPIE* 3677, pp. 159–168 (1999), the most widely studied have been the angular, or '2-Θ' (because of the two theta variables shown in FIG. 1) variety where, as mentioned earlier, the incident angle is varied in order to obtain a scatter signature. It is this type of scatterometer that is preferred, but not necessary, for the measurement of line profile asymmetry. It should be noted that the scanning optical system in FIG. 1 allows this angular scatterometer to measure both positive and negative angles from normal incidence (0 degrees) up to approximately +/−47 degrees.

Several different approaches have also been explored for the solution of the inverse problem. C. J. Raymond, et al. (1995), supra; R. H. Krukar, Ph.D. Dissertation, University of New Mexico (1993); J. Bischoff, et al., *Proc SPIE* 3332, pp. 526–537 (1998); and I. J. Kallioniemi, et al., *Proc SPIE* 3743, pp. 33–40 (1999). Because the optical response of a diffraction grating can be rigorously simulated from Maxwell's equations, the most common methods are model-based analyses. These techniques rely on comparing the measured scatter signature to signatures generated from a theoretical model. Both differential and integral models have been explored. Because these diffraction models are computationally intensive, standard regression techniques generally cannot currently be utilized without introducing errors due to the performance of the regression, but if the errors are small or tolerable, a regression approach could be used. Generally, however, the model is used a priori to generate a series of signatures that correspond to discrete iterations of various grating parameters, such as its thickness and the width of the grating lines. The set of signatures that results when all parameters are iterated over some range of values is known as a signature library. When the scatter signature is measured, it is compared against the library to find the closest match. Standard Euclidean distance measures, such as minimizing the mean square error (MSE) or root mean square error (RMSE), are used for identifying the closest match. The parameters of the modeled signature that agrees most closely with the measured signature are taken to be the parameters of this measured signature. The scatterometer preferably employed to practice the invention comprises analysis software based on error minimization.

In previous research scatterometry has been used for the measurement of critical dimensions (CDs) and profile characterization of photoresist samples, C. J. Raymond, et al. (1995), supra; and C. Baum, et al., "Resist line width and profile measurement using scatterometry," *SEMATECH AEC-APC Conference*, Vail, Colo., (September 1999), as well as etched materials such as poly-silicon and metals, S. Bushman, et al., "Scatterometry Measurements for Process Monitoring of Polysilicon Gate Etch," *Process, Equipment, and Materials Control in Integrated Circuit Manufacturing III, Proc. SPIE* 3213 (1997); C. Baum, et al., "Scatterometry for post-etch polysilicon gate metrology," *Integrated Circuit Metrology, Inspection and Process Control XIII, Proc. SPIE* 3677, pp. 148–158 (1999); and C. Raymond, et al., "Scatterometry for the measurement of metal features," *Integrated Circuit Metrology, Inspection and Process Control XIV, Proc. SPIE* 3998, pp. 135–146 (2000). Because the technology is rapid, non-destructive and has demonstrated excellent precision, it is an attractive alternative to other metrologies used in mainstream semiconductor manufacturing. In particular, scatterometry is quite amenable to measurements of asymmetry because, as will be demonstrated, angular scatter 'signatures' can quickly show (without performing the inverse problem) if any asymmetry is present on the grating lines.

Figure 2:
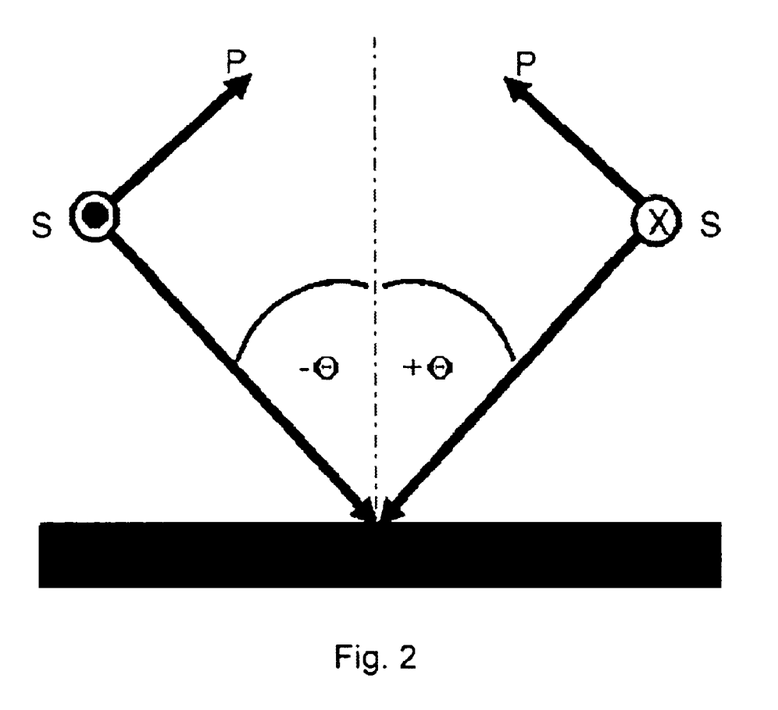
FIG. 2 illustrates the geometry of the angular scatterometry measurement employed by the invention.

When considering whether or not to expect symmetry in the measured diffraction efficiency of the specular (zero order) scatter signature it is convenient to decompose both the input and output fields into S and P components relative to the input boundary of the grating problem (in this case the xy-plane). FIG. 2 illustrates the geometry of these components relative to the angular scan direction (scans from both the positive and negative angular regions are shown). Note that the plane of incidence shown in this figure is the page itself, and no reference has yet been made with respect to the orientation of the grating relative to this plane of incidence. From the figure we can see that there is a phase difference in the S polarization component when the beam moves from one half of the angular region to the other. This phase difference is one reason why an asymmetric angular signature can be produced from an asymmetric line profile.

Figure 3A:
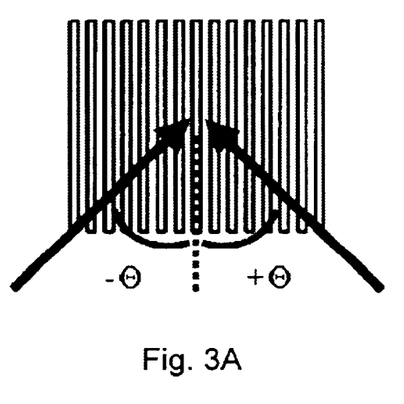
FIGS. 3(a) and (b) illustrate, respectively, so-called conventional and conical scatterometry measurement orientations.
Figure 3B:
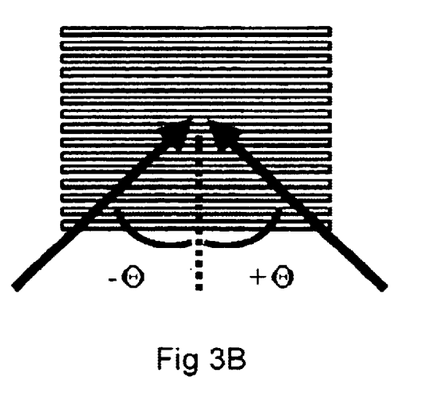

Grating orientation relative to the plane of incidence is another important consideration in the measurement of sample asymmetry. FIG. 3 depicts two orientations, known as the conical and conventional configurations. From first principles it can be shown that a scan parallel to the grating vector (the so-called 'normal' or 'conventional' configuration) is the only case which never couples the S and P modes of the total electromagnetic field (see, for example, equation (48) of M. Mihama, et al., "Formulation for stable and efficient implementation of the rigorous coupled-wave analysis of binary gratings," *J. Opt. Soc. Amer. A*, Vol. 12, pp. 1068–1076 (May 1995)). For general conical scattering problems, if the input illumination is in a pure P-polarization state the coupled nature of the problem tells one that one may observe both S and P components in the output (total) field. Similarly, if the input illumination is in a pure S-polarization state then we may observe both S and P components in the output (total) field.

The scattering problem is linear and so the principle of superposition holds. If a mixed polarization state is used for the input wave we may decompose the input field into S and P components, solve the problems separately, and then superpose the resulting output fields in complex amplitude. The S component of the total output field is composed of contributions from both the S and P portions of the input field due to the fully coupled nature of the problem. A similar statement is true of the P component of the total output field. The superposition takes place in complex amplitude and thus field components in the S-polarization state coming from S and P portions of the input field exhibit interference effects. This means that relative phase differences between the S and P components of the total input field can translate into amplitude differences in the S and P components of the total output field. With this in mind one expects asymmetry in output diffraction efficiencies for any case where coupling is present. It should also be noted that in a strict conical scan (the wave vector of the illuminating beam remains parallel to the structure's plane of symmetry), a symmetric structure produces no coupling. Hence, for this case one expects symmetry in the measured diffraction efficiencies. Only in the case of an asymmetric structure or a general conical scan (the wave vector of the illuminating beam does not remain parallel to the structure's plane of symmetry) with both S and P components present in the input beam does one expect asymmetry in the measured S and P diffraction efficiencies.

Figure 4A:
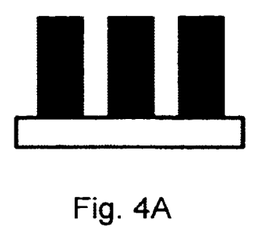
FIGS. 4(a)–(c) illustrate, respectively, a symmetric and two asymmetric resist profiles.
Figure 4B:
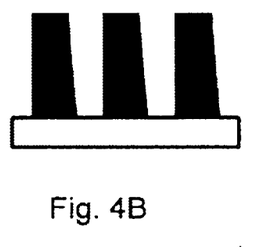
Figure 4C:
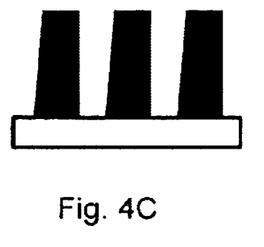
Figure 5:
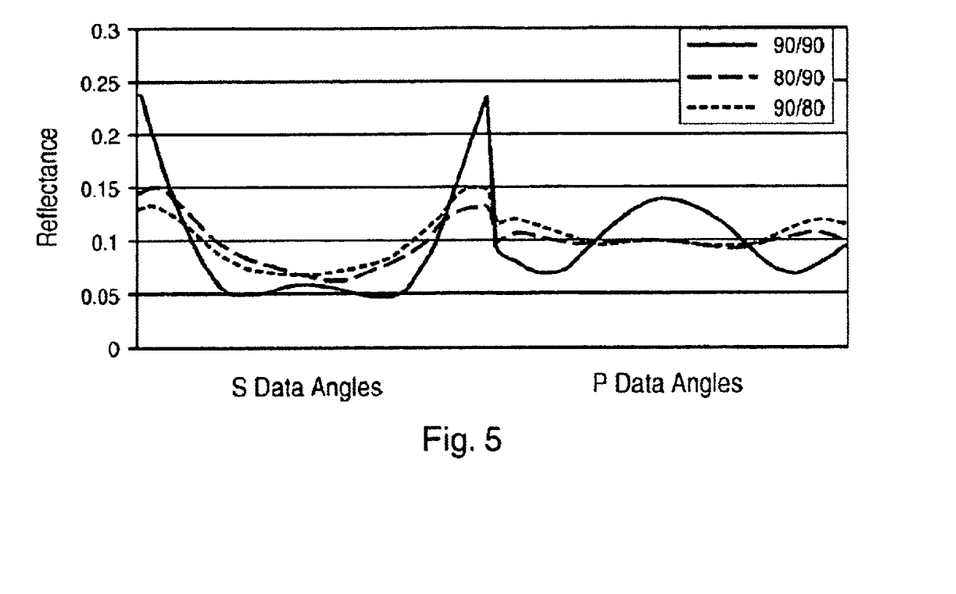
FIG. 5 is a graph of angular signature data corresponding to the profiles of FIGS. 4(a)–(c)

To introduce this concept of asymmetric grating lines giving rise to asymmetric measured scatter signatures consider the simple photoresist line profiles shown in FIGS. 4(a)–(c). FIG. 4(a) depicts a perfectly symmetric profile with both wall angles equal to 90 degrees. In FIG. 4(b), the right wall angle has been changed to 80 degrees, while in FIG. 4(c) the opposite case is illustrated (left at 80 degrees, right back to 90 degrees). FIG. 5 shows the angular scatter signatures—measured through complementary angles—associated with each of these profiles. As can be seen in the figure, the symmetric profile yields a symmetric scatter signature for both polarizations. However, the asymmetric profiles show a significant amount of asymmetry in both polarizations. In fact, the signatures appear to be skewed, or 'tipped,' as a result of the profile asymmetry. Furthermore, a comparison of the signature data for the 80/90 and 90/80 degree cases shows an interesting result—the reversal of the sidewall angles yields a reversal of the signature. Physically this reversal would be the same as rotating the wafer through 180 degrees and thereby transposing the positive and negative regions of the scan, so this result is self consistent. These figures also illustrate the advantage of angular scatterometry for determining the presence of asymmetry since one could establish that the profiles were non-symmetric with mere visual investigation of the signatures. However, if only 'half-sided' (positive or negative) angles were present, or if the system was a spectral scatterometer operating at a fixed angle, asymmetry could be determined by performing the solution to the inverse problem (i.e., performing the model comparison, either by way of a regression or through the use of a library comparison).

The examples below show that the scatterometry technique of the invention has good sensitivity for measuring line asymmetry, and can therefore be used for qualifying processes for which symmetric results might be desired, such as lithography and etch processing. Comparisons with other measurement technologies such as AFM and cross-section SEM show good consistency.

INDUSTRIAL APPLICABILITY

The invention is further illustrated by the following non-limiting examples.

To assess the viability of performing asymmetric profile measurements using scatterometry three different sample types were investigated (Examples 1–3). The first sample set was comprised of three wafers of photoresist lines on a metal substrate. The second sample was a single wafer of etched poly-Si. The third set was also a single wafer of grating lines printed in 193 nm photoresist. For each sample set the raw scatter signatures were obtained by performing measurements in a conical scanning orientation and through positive and negative angles. Suitable scatterometry libraries were generated for each sample set and included independent left and right variation in sidewall as well as the other parameters such as CD and thickness.

Example 4 illustrates the use of the invention to measure alignment of two successive layers on a semiconductor wafer.

EXAMPLE 1

Photoresist Lines on Metal Substrate

The linewidths for this sample set were nominal 250 nm in width. The stack composition, from the top down, was comprised of the patterned photoresist on ARC on a TiN layer, followed by a thick AlCu layer (this effectively acted as the substrate).

Figure 6:
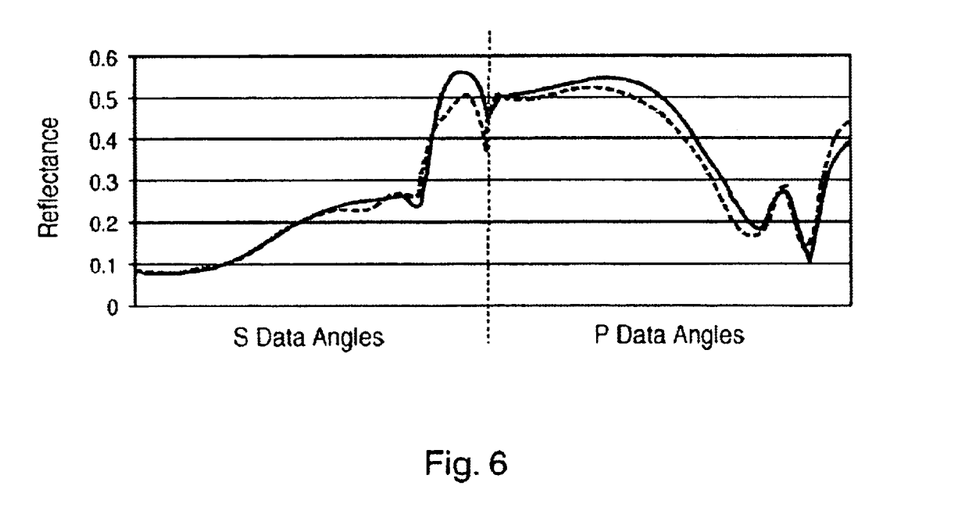
FIG. 6 is a graph of an angular scatterometry signature (mirrored) from metal resist wafers.

The raw signatures from this sample set showed a good deal of asymmetry. FIG. 6 depicts one signature from this data set with the positive and negative halves of the angular scan superimposed ('mirrored') on top of one another. Clearly, as the figure illustrates, the two halves are not the same. In fact, they differ at some angles by more than 5% in terms of reflectivity, and the structure of the signature differs at some angles as well. Because the measurements were made in the conical grating orientation, this is a sign of profile asymmetry.

Figure 7:
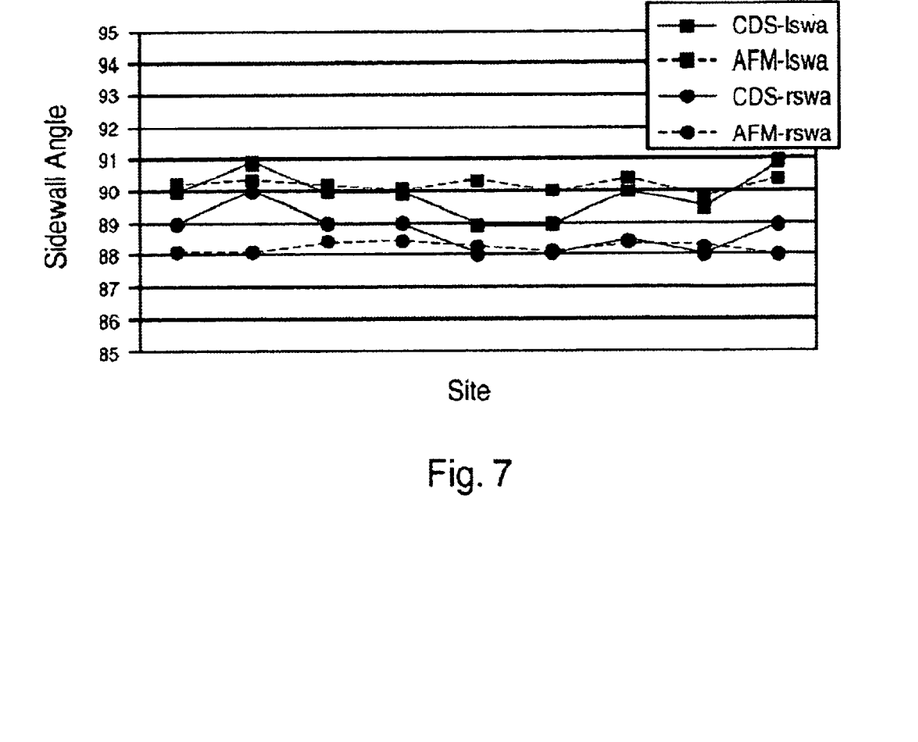
FIG. 7 is a graph of sidewall angle results from wafer 5 of the resist-on-metal sample set.

The raw signatures from this data set matched well to the model. Sidewall angle results from these wafer measurements can be seen in FIG. 7. Recall that the library allowed for independent variation in the left and right sidewall angles. In addition to the scatterometry measurements, AFM data from the same sites can be seen on this plot. Both the AFM and scatterometer results indicate that there is indeed a difference in the sidewall angles, and that it is in the range of 1–2 degrees. The data both agree that the left wall angle is steeper than the right wall angle as well. The scatterometry data indicate that the left and right angles move in tandem, i.e., that the overall width of the line does not change but rather 'sways' by 1–2 degrees from site to site across the wafer. This effect could be due to correlation between the left and right wall angle parameters, but a check of the modeled signature data revealed that they are quite distinct when one wall angle is left fixed and the other allowed to vary.

EXAMPLE 2

Etched Poly-Si Lines

Figure 8:
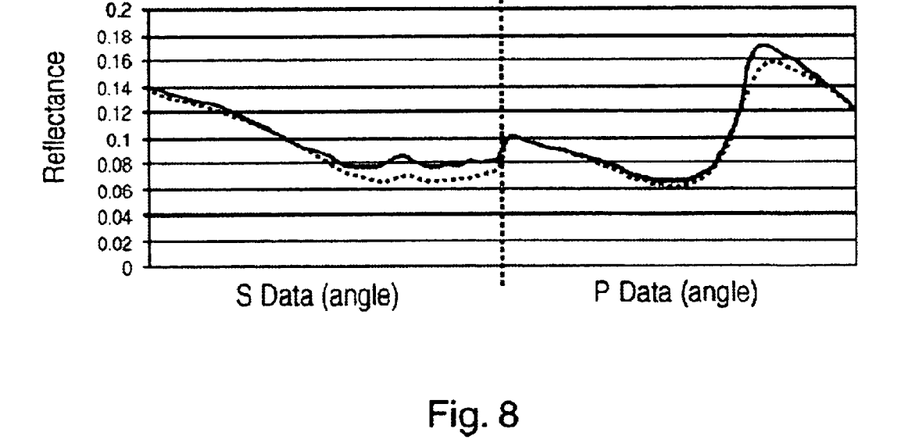
FIG. 8 is a graph of an angular scatterometry signature (mirrored) from an etched poly-silicon wafer.

The linewidths for this sample set ranged from 150 to 300 nm. The stack was comprised of patterned (etched) poly-Si on oxide on Si substrate. The raw signatures from this sample set showed a slight amount of asymmetry when measured in the conical configuration. FIG. 8 depicts one such signature with both the positive and negative halves of the signature 'mirrored' to illustrate this asymmetry.

Figure 9A:
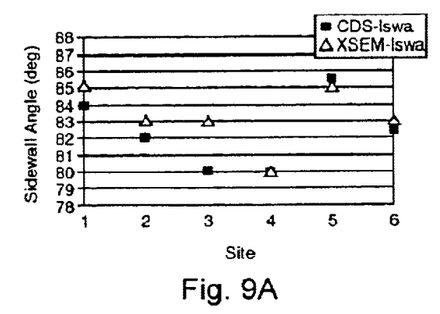
FIGS. 9(a) and (b) are, respectively, left and right sidewall angle comparisons between scatterometry and cross-section SEM for the etched poly-silicon wafer.
Figure 9B:
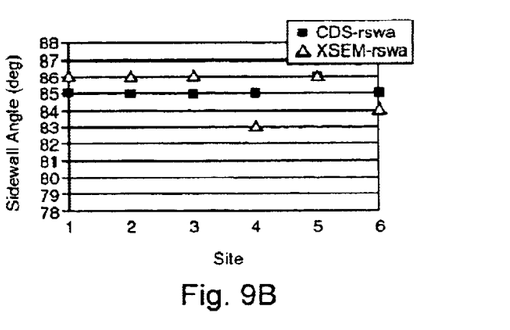

In order to draw comparisons, the wafer used for these scatterometry measurements was cross-sectioned and measured by a SEM to determine the sidewall angles of the lines. FIG. 9 shows the results of comparing the left and right sidewall angle measurements of the two technologies. As the figure illustrates, both tools are reporting some degree of sidewall asymmetry, with the left wall angle being generally smaller. Furthermore, the sidewall angle correlation between the two techniques is good and shows similar trending from site to site.

EXAMPLE 3

193 nm Photoresist Lines

The last sample set investigated was a single wafer of 193 nm photoresist lines printed on a BARC layer, a poly layer, an oxide layer and a silicon substrate. The nominal feature sizes on this wafer were 180 nm lines.

Figure 10:
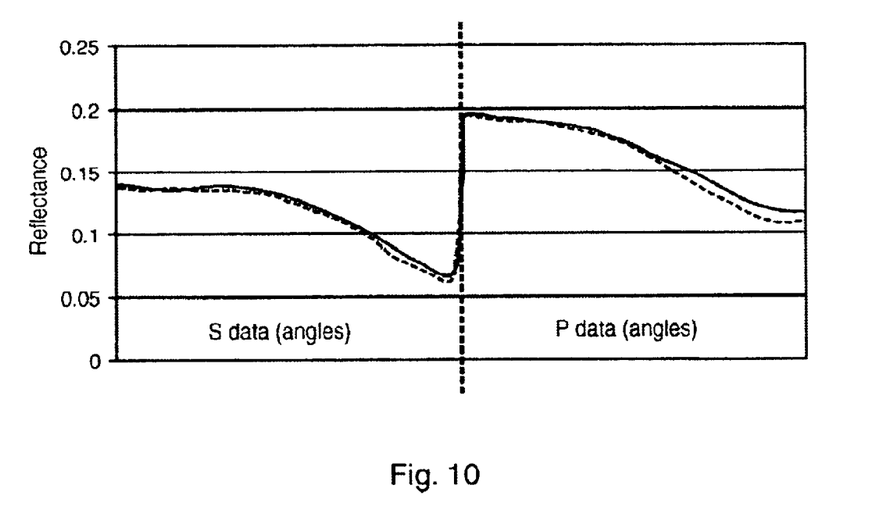
FIG. 10 is a graph of an angular scatterometry signature (mirrored) from a 193 nm resist wafer.

For this wafer, the signature data was only mildly asymmetric when measured in conical mode. FIG. 10 depicts the S and P polarizations for one of these signatures 'mirrored' back upon itself. In contrast to the signature asymmetries observed from the previous samples, this asymmetry was relatively weak.

Figure 11A:
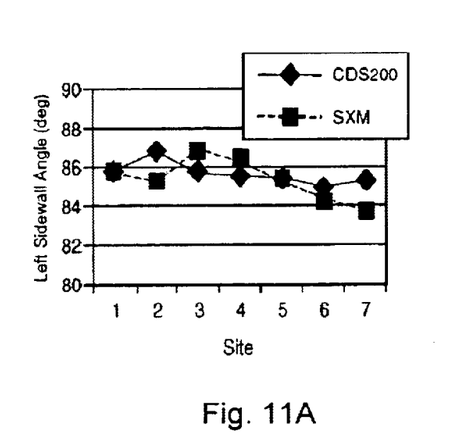
Figure 11B:
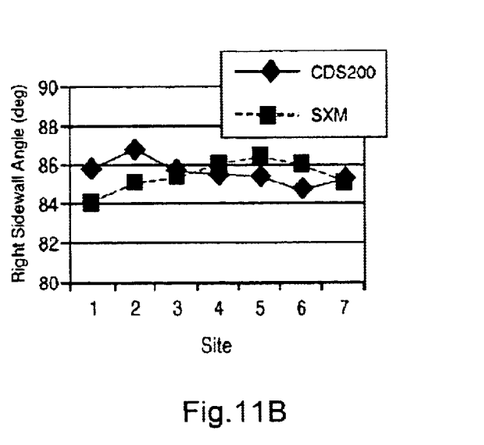
Figure 12:
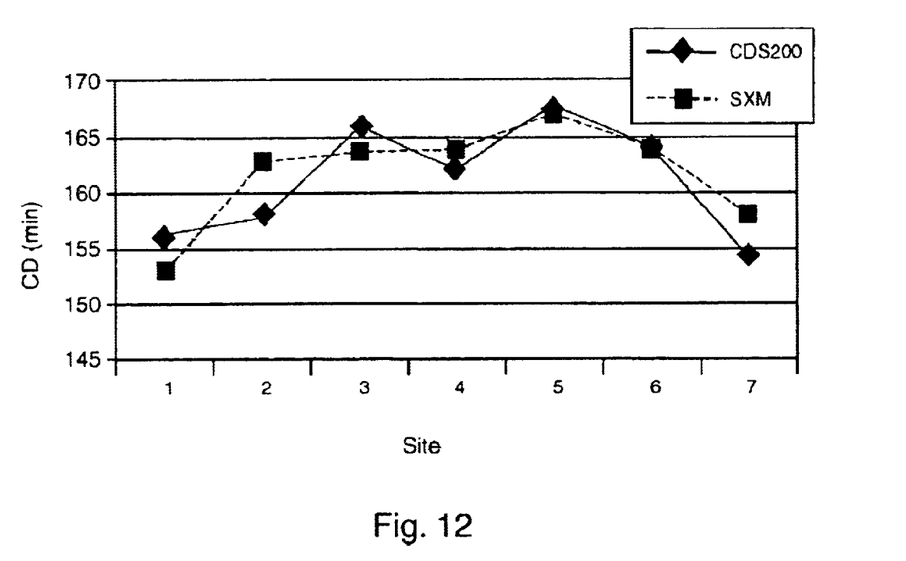
FIG. 12 is a comparison of AFM and scatterometry CD measurements for the 193 nm resist wafer.

The left and right wall angle data for one row from this wafer can be seen in FIG. 11. Included on the plots in this figure are measurements made on the same sites with an AFM. Both measurement technologies agree well in terms of the overall magnitude of the wall angles. The AFM data shows more asymmetric measurements but are generally consistent with the data from the scatterometer. A comparison of the CD measurements obtained by the scatterometer and AFM from this same row can be seen in FIG. 12. As this figure shows, the agreement between the AFM and scatterometer measurements is excellent. The average difference between these two techniques is 2.43 nm.

EXAMPLE 4

Successive Layer Alignment Measurement

The alignment of two successive layers on a semiconductor wafer is critical for the ultimate performance of the devices being manufactured. This alignment (also called overlay) is so important that there are tools dedicated to performing this one task. These tools are based on measuring images of special alignment marks printed at each layer. As the semiconductor industry moves towards smaller and smaller dimensions, however, there is a great deal of doubt surrounding the ability of these tools to provide the necessary measurement resolution.

Scatterometry is a technology well-suited for overlay measurements. By using a grating-on-grating structure, scatterometry measurements of the $0^{th}$, or specular, diffraction order are sensitive to alignment shifts in the successive grating layers. This shift in the grating layer (also referred to as an offset) results in an asymmetric line profile, and that can be measured using a scatterometer in the proper measurement orientation, and preferably (though not necessarily) with the ability to measure complementary angles (both positive and negative angles).

Figure 13:
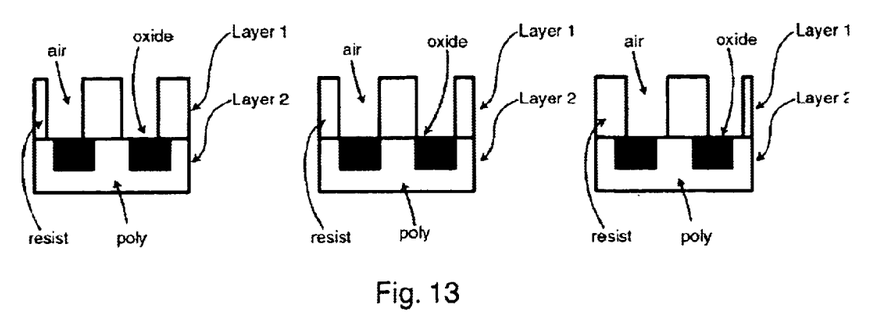
FIG. 13 shows images of a grating-on-grating profile that can be used for measurement of overlay misalignment.
Figure 14:
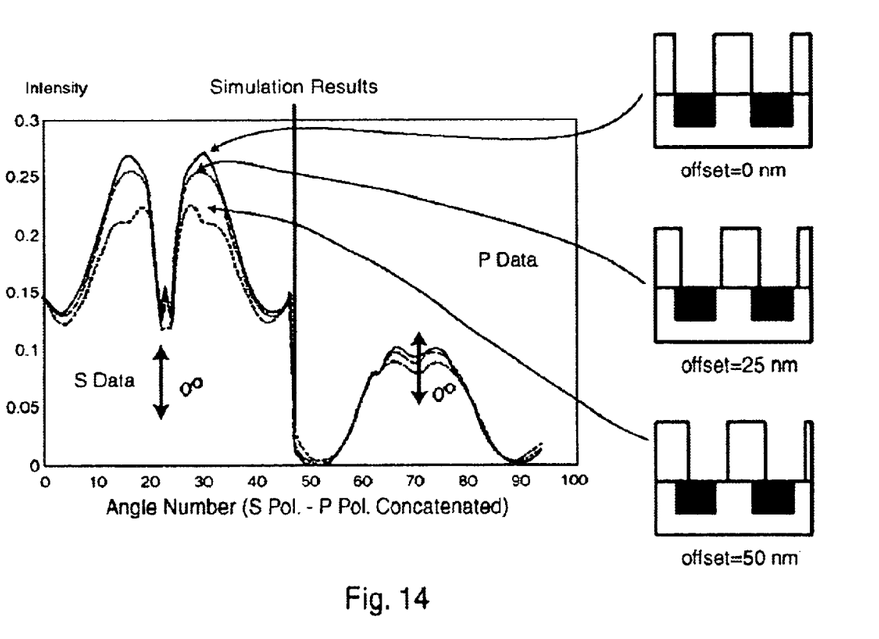
FIG. 14 is a graph of angular scatterometry signatures for the profiles of FIG. 14 employing a conventional (non-conical) scan.
Figure 15:
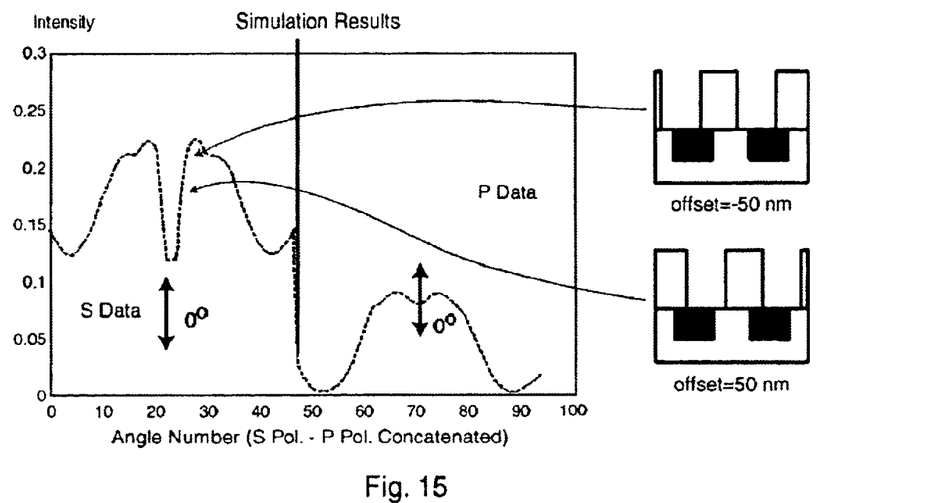
FIG. 15 is a graph of (non-unique) angular scatterometry signatures for left and right offsets employing a conventional scan.

FIG. 13 present images of a grating-on-grating profile that can be used for the measurement of overlay. Errors in aligning the two successive layers results in a shift between the grating lines, and an asymmetric line profile. FIG. 14 present results that demonstrate sensitivity to offsets or overlay errors for measurements performed in the conventional orientation (see FIG. 3(*a*)). The signatures change when offsets are introduced, which is a positive sign for general measurement sensitivity. However, as shown in FIG. 15, for a conventional scan the signatures that result when same magnitude +/− offsets are introduced are not unique. Hence, a conventional scan is less desirable than a conical scan.

Figure 16:
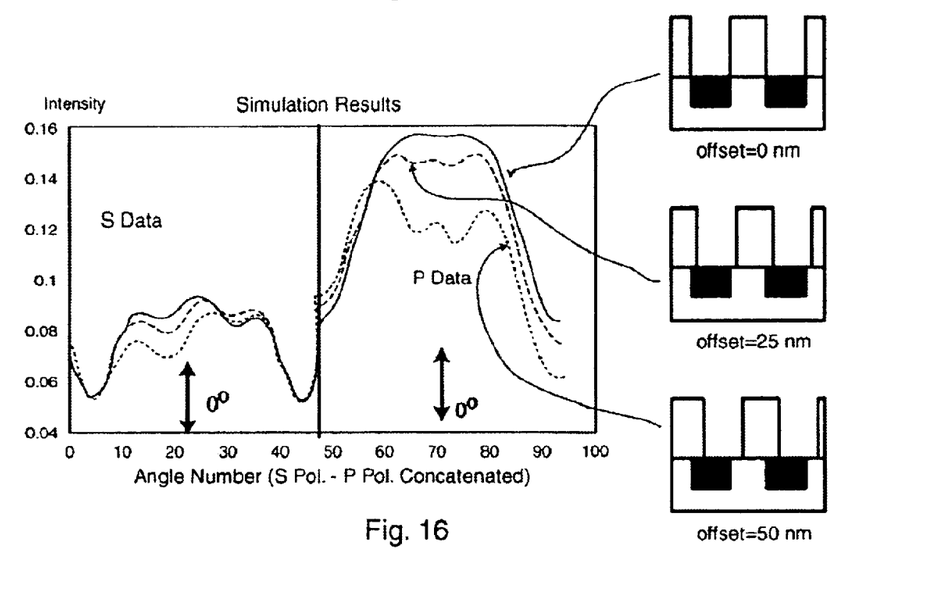
FIG. 16 is a graph of angular scatterometry signatures for the profiles of FIG. 14 employing a conical scan.
Figure 17:
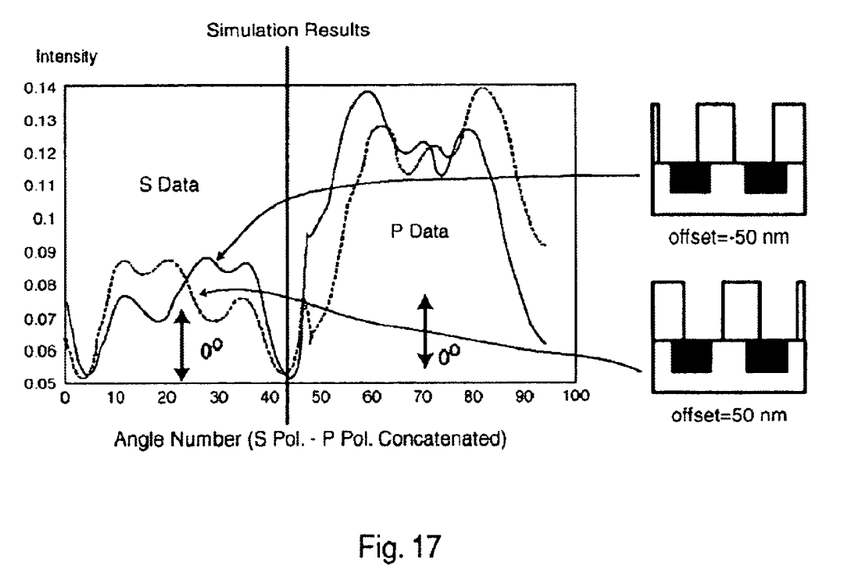
FIG. 17 is a graph of (unique) angular scatterometry signatures for left and right offsets employing a conical scan.

Repeating the exercise with conical scans results in the signatures shown in FIGS. 16 and 17. As with conventional scans, FIG. 16 shows signature changes with offset, but FIG. 17 shows that changes are now unique as between +/− (left/right) offsets. Also note the symmetry about zero degrees.

Accordingly, investigation has shown that conventional and conical scans of the specular ($0^{th}$) order are both sensitive to offsets, but only conical scans provide unique signatures with respect to left/right shifts. Existing scatterometry methods for assessing overlays involve use of $1^{st}$ and higher orders and so require special measurement hardware to measure higher orders. See, e.g., Sohail Naqvi, et al., "Diffractive techniques for lithographic process monitoring and control", JVSTB 12(6) (November 1994) (moire interferometric technique using higher orders); and J. Bischoff, et al., "Light diffraction based overlay measurement", Proc. SPIE Vol. 4344, pp. 222–233 (2001) ($1^{st}$ order measurement of grating-in-grating).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of measuring line profile asymmetries in microelectronic devices, the method comprising the steps of:
    directing light at an array of microelectronic features of a microelectronic device;
    detecting light scattered back from the array comprising one or more features selected from the group consisting of one or more angles of reflection and one or more wavelengths; and
    comparing one or more characteristics of the back-scattered light by performing an operation comprising examining data from complementary angles of reflection.

2. The method of claim 1 wherein the directing step comprises directing light at substantially a single wavelength.

3. The method of claim 1 wherein the directing step comprises directing light at a plurality of wavelengths.

4. The method of claim 1 wherein the comparing step comprises comparing light intensity.

5. The method of claim 1 wherein the comparing step additionally comprises comparing phase.

6. The method of claim 1 wherein the comparing step additionally comprises comparing ratios of light magnitude and light phase.

7. The method of claim 1, 2 or 3 wherein the directing step comprises directing light at an array of microelectronic features in general conical configuration.

8. The method of claim 1, 2 or 3 wherein the directing and detecting steps are performed by an angular scatterometer.

9. The method of claim 1, 2 or 3 wherein the directing and detecting steps are performed by a spectral scatterometer.

10. The method of claim 1, 2 or 3 wherein the comparing step comprises decomposing back-scattered light into S and P components relative to a plane of incidence.

11. The method of claim 1, 2 or 3 wherein the detecting step comprises detecting specular order diffracted light.

12. The method of claim 1, 2 or 3 additionally comprising the step of employing the results of the comparing step to detect asymmetries selected from the group consisting of asymmetries within a single layer of the microelectronic device and asymmetries within multiple layers of the microelectronic device.

13. The method of claim 12 additionally comprising the step of controlling a manufacturing process if results of the comparing step indicate an asymmetry in the array.

14. An apparatus for measuring line profile asymmetries in microelectronic devices, said apparatus comprising:

means for directing light at an array of microelectronic features of a microelectronic device;

means for detecting light scattered back from the array comprising one or more features selected from the group consisting of one or more angles of reflection and one or more wavelengths; and means for comparing one or more characteristics of the back-scattered light by performing an operation comprising examining data from complementary angles of reflection.

15. The apparatus of claim 14 wherein said directing means comprises means for directing light at substantially a single wavelength.

16. The apparatus of claim 14 wherein said directing means comprises means for directing light at a plurality of wavelengths.

17. The apparatus of claim 14 wherein said comparing means additionally comprises means for comparing light intensity.

18. The apparatus of claim 14 wherein said comparing means additionally comprises means for comparing phase.

19. The apparatus of claim 14 wherein said comparing means additionally comprises means for comparing ratios of light magnitude and light phase.

20. The apparatus of claim 14, 15 or 16 wherein said directing means comprises means for directing light at an array of microelectronic features in general conical configuration.

21. The apparatus of claim 14, 15 or 16 wherein said directing and detecting means comprise an angular scatterometer.

22. The apparatus of claim 14, 15 or 16 wherein said directing and detecting means comprise a spectral scatterometer.

23. The apparatus of claim 14, 15 or 16 wherein said comparing means comprises means for decomposing back-scattered light into S and P components relative to a plane of incidence.

24. The apparatus of claim 14, 15 or 18 wherein said detecting means comprises means for detecting specular order diffracted light.

25. The apparatus of claim 14, 15 or 16 additionally comprising means for employing the results of the comparing step to detect asymmetries selected from the group consisting of asymmetries within a single layer of the microelectronic device and asymmetries within multiple layers of the microelectronic device.

26. The apparatus of claim 25 additionally comprising means for controlling a manufacturing process if said comparing means indicates an asymmetry in the array.

27. A method of measuring line profile asymmetries in microelectronic devices, the method comprising the steps of:

directing light at an array of microelectronic features of a microelectronic device;

detecting light scattered back from the array comprising one or more features selected from the group consisting of one or more angles of reflection and one or mare wavelengths; and comparing one or more characteristics of the back-scattered light by performing an operation comprising performing a model comparison with an asymmetric model.

28. The method of claim 27 wherein the directing step comprises directing light at substantially a single wavelength.

29. The method of claim 27 wherein the directing step comprises directing light at a plurality of wavelengths.

30. The method of claim 27 wherein the comparing step comprises comparing light intensity.

31. The method of claim 27 wherein the comparing step additionally comprises comparing phase.

32. The method of claim 27 wherein the comparing step additionally comprises comparing ratios of light magnitude and light phase.

33. The method of claim 27 wherein comparing comprises a model comparison with a library of asymmetric models.

34. The method of claim 27 wherein comparing comprises a model comparison by regression analysis with an asymmetric model.

35. The method of claim 27, 28 or 29 wherein the directing step comprises directing light at an array of microelectronic features in general conical configuration.

36. The method of claim 27, 28 or 29 wherein the directing and detecting steps are performed by an angular scatterometer.

37. The method of claim 27, 28 or 29 wherein the directing and detecting steps are performed by a spectral scatterometer.

38. The method of claim 27, 28 or 29 wherein the comparing step comprises decomposing back-scattered light into S and P components relative to a plane of incidence.

39. The method of claim 27, 28 or 29 wherein the detecting step comprises detecting specular order diffracted light.

40. The method of claim 27, 28 or 29 additionally comprising the step of employing the results of the comparing step to detect asymmetries selected from the group consisting of asymmetries within a single layer of the microelectronic device and asymmetries within multiple layers of the microelectronic device.

41. The method of claim 40 additionally comprising the step of controlling a manufacturing process if results of the comparing step indicate an asymmetry in the array.

42. An apparatus for measuring line profile asymmetries in microelectronic devices, said apparatus comprising:

means for directing light at an array of microelectronic features of a microelectronic device;

means for detecting light scattered back from the array comprising one or more features selected from the group consisting of one or more angles of reflection and one or more wavelengths; and means for comparing one or more characteristics of the back-scattered light by performing an operation comprising performing a model comparison with an asymmetric model.

43. The apparatus of claim 42 wherein said directing means comprises means for directing light at substantially a single wavelength.

44. The apparatus of claim 42 wherein said directing means comprises means for directing light at a plurality of wavelengths.

45. The apparatus of claim 42 wherein said comparing means additionally comprises means for comparing light intensity.

46. The apparatus of claim 42 wherein said comparing means additionally comprises means for comparing phase.

47. The apparatus of claim 42 wherein said comparing means additionally comprises means for comparing ratios of light magnitude and light phase.

48. The apparatus of claim 42 wherein said means for comparing comprises a model comparison with a library of asymmetric models.

49. The apparatus of claim 42 wherein said means for comparing comprises a model comparison by regression analysis with an asymmetric model.

50. The apparatus of claim 42, 43 or 44 wherein said directing means comprises means for directing light at an array of microelectronic features in general conical configuration.

51. The apparatus of claim 42, 43 or 44 wherein said directing and detecting means comprise an angular scatterometer.

52. The apparatus of claim 42, 43 or 44 wherein said directing and detecting means comprise a spectral scatterometer.

53. The apparatus of claim 42, 43 or 44 wherein said comparing means comprises means for decomposing backscattered light into S and P components relative to a plane of incidence.

54. The apparatus of claim 42, 43 or 44 wherein said detecting means comprises means for detecting specular order diffracted light.

55. The apparatus of claim 42, 43 or 44 additionally comprising means for employing the results or the comparing step to detect asymmetries selected from the group consisting of asymmetries within a single layer of the microelectronic device and asymmetries within multiple layers of the microelectronic device.

56. The apparatus of claim 55 additionally comprising means for controlling a manufacturing process if said comparing means indicates an asymmetry in the array.

* * * * *